United States Patent
Bastiaensen et al.

(10) Patent No.: US 6,541,665 B1
(45) Date of Patent: Apr. 1, 2003

(54) METHOD FOR PURIFYING ACRYLIC ACID OR METHACRYLIC ACID BY CRYSTALLIZATION AND DISTILLATION

(75) Inventors: Erik Bastiaensen, Kapellen (BE); Bernd Eck, Viernheim (DE); Joachim Thiel, Neustadt (DE)

(73) Assignee: BASF Aktiengesellschaft, Ludwigshafen (DE)

( * ) Notice: Subject to any disclaimer, the term of this patent is extended or adjusted under 35 U.S.C. 154(b) by 0 days.

(21) Appl. No.: 09/719,572

(22) PCT Filed: Jun. 30, 1999

(86) PCT No.: PCT/EP99/04516

§ 371 (c)(1), (2), (4) Date: Jan. 2, 2001

(87) PCT Pub. No.: WO00/01657

PCT Pub. Date: Jan. 13, 2000

(30) Foreign Application Priority Data

Jul. 1, 1998 (DE) .......................................... 198 29 477

(51) Int. Cl.$^7$ .......................... C07C 51/43; C07C 51/42
(52) U.S. Cl. ...................................... 562/600; 562/545
(58) Field of Search .................................. 562/600, 545

(56) References Cited

U.S. PATENT DOCUMENTS

| 5,504,247 A | | 4/1996 | Saxer et al. |
|---|---|---|---|
| 5,523,480 A | * | 6/1996 | Bauer et al. |
| 5,831,124 A | * | 11/1998 | Machhammer et al. |
| 6,433,222 B1 | * | 8/2002 | Eck et al. ................. 562/600 |

FOREIGN PATENT DOCUMENTS

| DE | A 196 06 877 | 2/1996 |
|---|---|---|
| EP | 0 616 998 | 9/1994 |
| EP | 0 675 100 A | 10/1995 |
| EP | 0 729 867 A | 9/1997 |
| WO | WO 98/01415 A | 1/1998 |

* cited by examiner

*Primary Examiner*—Shailendra Kumar
(74) *Attorney, Agent, or Firm*—Oblon, Spivak, McClelland, Maier & Neustadt, P.C.

(57) ABSTRACT

In a process for the purification of acrylic acid or methacrylic acid by crystallization and distillation, the following steps are carried out:

(a) crystallization of a mixture containing the acrylic acid or methacrylic acid with formation of product crystals having a higher concentration of acrylic acid or methacrylic acid and of a mother liquor, (b) distillation of at least part of the mother liquor from step (a) with formation of a distillation residue, which is at least partly removed, and of a top product, (c) crystallization of at least part of the top product from step (b) with formation of a crystallization residue, which is removed, and of crystals and (d) recycling of the crystals from step (c) to the crystallization (a).

20 Claims, 1 Drawing Sheet

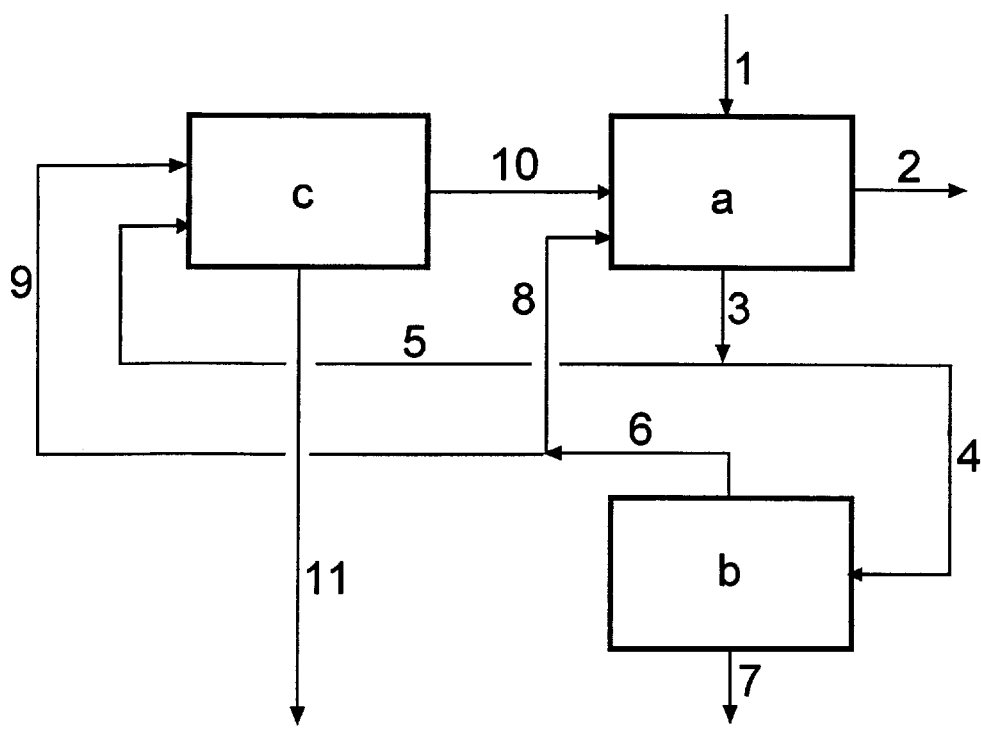

METHOD FOR PURIFYING ACRYLIC ACID OR METHACRYLIC ACID BY CRYSTALLIZATION AND DISTILLATION

The present invention relates to a process for the purification of acrylic acid or methacrylic acid by a combination of crystallization and distillation.

Acrylic acid is an important key chemical. Owing to its very reactive double bond and the acid function, it is particularly suitable as a monomer for the preparation of polymers, for example for adhesives, dispersions, surface coatings or superabsorbers.

It is generally known that acrylic acid can be prepared via acrolein by gas-phase oxidation of propene with molecular oxygen under heterogeneous catalysis over catalysts present in the solid state at from 200 to 400° C. in two stages. Here, oxidic multicomponent catalysts, for example based on the oxides of the elements molybdenum, bismuth and iron (in the first stage) or molybdenum and vanadium (in the second stage) are used.

DE-A-196 06 877 describes a process for the preparation of acrylic acid or methacrylic acid, in which a product mixture containing the acrylic acid or methacrylic acid and prepared by catalytic gas-phase oxidation is absorbed with a high-boiling solvent, the laden solvent is separated into the solvent and a crude acid by distillation and the acrylic acid or methacrylic acid is obtained from the crude acid by crystallization.

EP-A-0 616 998 relates to a process for the purification of acrylic acid by means of fractional crystallization by a combination of dynamic and static crystallization in a plurality of stages, the residue of the dynamic crystallization being further purified by the static crystallization and the acrylic acid obtained being recycled to the dynamic crystallization.

EP-A-0 675 100 discloses a process for the preparation of $\alpha,\beta$-unsaturated $C_3$–$C_6$-carboxylic acids and of acrylic acid, in which the acid is prepared by oxidative dehydrogenation of the corresponding saturated acid, the dehydrogenation product is crystallized from the melt, the mother liquor obtained is subjected to fractional distillation and the top product of the distillation is recycled to the dehydrogenation reactor and the bottom product of the distillation to the melt crystallization or the top product is recycled to the melt crystallization and the bottom product to the dehydrogenation reactor. In a further embodiment of EP-A-0 675 100, the product stream obtained in the oxidative dehydrogenation is first subjected to fractional distillation, the top product of the distillation is recycled to the dehydrogenation reactor and the bottom product of the distillation is fed to a melt crystallization and the mother liquor obtained in the melt crystallization is then recycled to the distillation.

It is an object of the present invention to provide a process in which acrylic acid or methacrylic acid is obtained in high purity and in high yield.

We have found that this object is achieved by the combined use of crystallization and distillation, the mother liquor formed in a first crystallization of the mixture containing acrylic acid or methacrylic acid being fed at least partly to a distillation, the resulting top product being subjected at least partly to further crystallization and the resulting crystals in turn being recycled to the first crystallization.

The present invention therefore relates to a process for the purification of acrylic acid or methacrylic acid by crystallization and distillation, which comprises the following steps:

(a) crystallization of a mixture containing the acrylic acid or methacrylic acid with formation of product crystals having a higher concentration of acrylic acid or methacrylic acid and of a mother liquor, (b) distillation of at least part of the mother liquor from step (a) with formation of a distillation residue, which is at least partly removed, and of a top product, (c) crystallization of at least part of the top product from step (b) with formation of a crystallization residue, which is removed, and of crystals and (d) recycling of the crystals from step (c) to the crystallization (a).

Preferred embodiments of the invention are defined in the following description, the subclaims, the figure and the example.

The FIGURE shows a preferred embodiment for carrying out the novel process.

The mixture containing, according to the invention, acrylic acid or methacrylic acid is not subject to any special restrictions. Preferably used mixtures are those which contain from 50 to 99.95, preferably from 60 to 98, in particular from 75 to 95,% by weight of acrylic acid or methacrylic acid, based in each case on 100% by weight of mixture. The type of compounds, impurities or secondary components present in addition to the acrylic acid or methacrylic acid is not subject to any restriction. These are preferably compounds or secondary components formed in the catalytic gas-phase oxidation to give acrylic acid or methacrylic acid, e.g. water, acrolein, methacrolein, acetic acid, propionic acid, formaldehyde or other aldehydes. They may also be solvents in which the product mixture formed in the catalytic gas-phase oxidation to give acrylic acid or methacrylic acid is absorbed. Furthermore, the mixture containing the acrylic acid or methacrylic acid may contain polymerization inhibitors or process stabilizers as secondary components, these preferably being a stabilizer such as phenothiazine or another stabilizer described in EP-A-0 765 856. Such stabilizers are added to the acrylic acid or methacrylic acid after their preparation in order as far as possible to inhibit the polymerization of the acid in the purification of the acid in the subsequent process steps.

In a preferred embodiment of the invention, the mixture containing the acrylic acid or methacrylic acid is prepared by catalytic gas-phase oxidation of $C_3$- or C4-alkanes, -alkenes, -alkanols and/or -alkanals and/or precursors thereof. Particularly advantageously, the mixture is prepared by catalytic gas-phase oxidation of propene, acrolein, tert-butanol, isobutene, isobutane, isobutyraldehyde, methacrolein, isobutyric acid or methyl tert-butyl ether. Suitable starting compounds are all precursors of said compounds where the actual $C_3/C_4$ starting compound is formed as an intermediate only during the gas-phase oxidation. Methyl tert-butyl ether or isobutyric acid may be mentioned by way of example for the preparation of the methacrylic acid.

The catalytic gas-phase reaction of propene and/or acrolein to acrylic acid with molecular oxygen by known processes is particularly advantageous, in particular as described in DE-A-1 962 431, DE-A-2 943 707, German Patent 1 205 502, EP-A-0 257 565, EP-A-0 253 409, German Published Application 22 51 364, EP-A-0 117 146, British Patent 1 450 986 and EP-A-0 293 224. Here, temperatures of from 200 to 450° C. and, if required, superatmospheric pressure are preferably employed. Preferably used heterogeneous catalysts are oxidic multicomponent catalysts based on the oxides of molybdenum, bismuth and iron in the first stage (oxidation of propene to acrolein)

and those based on the oxides of molybdenum and vanadium in the second stage (oxidation of acrolein to acrylic acid). If propane is used as a starting material, it can be converted into a propene/propane mixture by: catalytic oxydehydrogenation as described, for example, in Catalysis Today 24 (1995), 307–313 or U.S. Pat. No. 5,510,558; by homogeneous oxydehydrogenation as described, for example, in CN-A-1 105 352; or by catalytic dehydrogenation as described, for example, in EP-A-0 253 409, EP-A-0 293 224, DE-A-195 08 558 or EP-A-0 117 146. When a propene/propane mixture is used, propane acts as a diluent gas. Other suitable propene/propane mixtures are refinery propene (70% of propene and 30% of propane) or cracker propene (95% of propene and 5% of propane). In principle, propene/propane mixtures such as those mentioned above can be oxidized with oxygen or air or a mixture of oxygen and nitrogen of any composition to give acrolein and acrylic acid.

The conversion of propene into acrylic acid is highly exothermic. The reaction gas, which, in addition to the starting materials and products, advantageously contains an inert diluent gas, for example atmospheric nitrogen, one or more saturated $C_1$–$C_6$-hydrocarbons, in particular methane and/or propane, and/or steam, can therefore absorb only a small part of the heat of reaction. Although the type of reactors used is not subject to any restriction per se, tube-bundle heat exchangers which are filled with the oxidation catalyst are generally used since in them the predominant part of the heat evolved during the reaction can be removed by convection and radiation to the cooled tube walls.

In the catalytic gas-phase oxidation, it is not pure acrylic acid which is obtained but a gaseous mixture which, in addition to the acrylic acid, may contain essentially unconverted acrolein and/or propene, steam, carbon monoxide, carbon dioxide, nitrogen, propane, oxygen, acetic acid, propionic acid, formaldehyde, further aldehydes and maleic anhydride as secondary components. Usually, the reaction product mixture contains from 1 to 30% by weight of acrylic acid, from 0.05 to 1% by weight of propene and from 0.05 to 1% by weight of acrolein, from 0.05 to 10% by weight of oxygen, from 0.05 to 2% by weight of acetic acid, from 0.01 to 2% by weight of propionic acid, from 0.05 to 1% by weight of formaldehyde, from 0.05 to 2% by weight of aldehydes, from 0.01 to 0.5% by weight of maleic anhydride and from 20 to 98, preferably from 50 to 98,% by weight of inert diluent gases, based in each case on the total reaction mixture. In particular, saturated $C_1$–$C_6$-hydrocarbons, for example from 0 to 90% by weight of methane and/or propane, as well as from 1 to 30% by weight of steam, from 0.05 to 15% by weight of carbon oxides and from 0 to 90% by weight of nitrogen, based in each case on 100% by weight of diluent gas, are present as inert diluent gases.

The methacrylic acid can be prepared analogously to acrylic acid, by catalytic gas-phase oxidation of $C_4$ starting compounds with molecular oxygen. The methacrylic acid is particularly advantageously obtainable, for example, by catalytic gas-phase oxidation of isobutene, isobutane, tert-butanol, isobutyraldehyde, methacrolein or methyl tert-butyl ether. The catalysts used are likewise transition metal mixed oxide catalysts (e.g. Mo, V, W and/or Fe). Particularly suitable processes are those in which the preparation is carried out starting from methacrolein, in particular when the methacrolein is produced by gas-phase catalytic oxidation of tert-butanol, isobutane or isobutene or by reaction of formaldehyde with propionaldehyde according to EP-B-0 092 097 or EP-B-0 058 927. It is thus also possible to prepare methacrylic acid in two stages by (1) condensation of propionaldehyde with formaldehyde (in the presence of a secondary amine as catalyst) to give methacrolein and (2) subsequent oxidation of the methacrolein to methacrylic acid.

As in the preparation of acrylic acid, it is not pure methacrylic acid that is obtained but a gaseous mixture which, in addition to the methacrylic acid, may contain essentially unconverted methacrolein and/or steam, carbon monoxide, carbon dioxide, nitrogen, oxygen, acetic acid, propionic acid, further aldehydes and maleic anhydride as secondary components. The novel process is used in particular when the reaction mixture contains from 0.02 to 2% by weight, based on the total reaction mixture, of methacrolein and otherwise essentially the same corresponding components as in the preparation of acrylic acid.

In a preferred embodiment, a crude acid as obtained by the abovementioned preparation by catalytic gas-phase oxidation and, according to DE-A-196 06 877, by subsequent absorption with a solvent and distillation is used as the mixture containing the acrylic acid or methacrylic acid.

The novel process is used in particular if the acid to be purified contains from 50 ppm to 2% by weight of maleic acid and/or maleic anhydride in addition to the abovementioned impurities.

The crystallization method used for the crystallization (a) and for the crystallization (c) is not subject to any restriction. It may be carried out continuously or batchwise, in one stage or a plurality of stages. In a preferred embodiment, one of the two crystallizations (a) or (c) is carried out as a fractional (multistage) crystallization or both crystallizations are carried out as said fractional crystallization. Usually, in fractional crystallization all stages which produce crystals which are purer than the mixture fed in and containing the acrylic acid or methacrylic acid are referred to as purification stages and all other stages are referred to as stripping stages. Expediently, multistage processes are operated here by the countercurrent principle, in which, after the crystallization in each stage, the crystals are separated from the mother liquor and these crystals are fed to the respective stage with the next highest purity, while the crystallization residue is fed to the respective stage with next lowest purity. In a preferred embodiment of the invention, the crystallization is carried out in apparatuses in which the crystals grow on cooled surfaces in the crystallization apparatus, i.e. are fixed in the apparatus (for example, dynamic layer crystal process from Sulzer Chemtech or static crystallization process from BEFS PROKEM). The crystallization may be carried out dynamically and/or statically, a combination of dynamic and static crystallization being particularly preferred. In the latter embodiment, as described in EP-A-0 616 998, the residue of the dynamic crystallization is preferably fed to the static crystallization and the crystals of the static crystallization are preferably fed to the dynamic crystallization. The method for carrying out the dynamic and/or static crystallization is not critical here. In the static crystallization, the liquid phase is agitated only by free convection, whereas in the dynamic crystallization the liquid phase is agitated by forced convection. The latter can be effected by forced flow in apparatuses with full flow-through (cf. for example German Laid-Open Application DOS 2,606,364) or by the application of a falling film to a cooled wall (cf. for example DT 1 769 123 and EP-A-0 218 545). Advantageously, the static crystallization is used in the stripping stages, in particular when the yield of the acid is to be further increased.

In a particularly preferred embodiment of the invention, the crystallization (a) is carried out as a dynamic crystallization and the crystallization (c) as a static crystallization.

In an advantageous embodiment of the invention, the crystallization is effected by cooling apparatus walls or by evaporating the solution under reduced pressure.

In the crystallization by cooling, the heat is removed by means of scraped-shell coolers which are connected to a stirred kettle or a container without a stirrer. The crystal suspension is circulated here by means of a pump. It is also possible to remove the heat via the wall of a stirred kettle by means of a stirrer passing close to the wall. A further preferred embodiment in the case of cooling crystallization is the use of cooling-disk crystallizers as produced, for example, by Gouda (The Netherlands). In a further suitable variant for crystallization by cooling, the heat is removed by means of conventional heat exchangers (preferably tube-bundle or plate-type heat exchangers). In contrast to scraped-shell coolers, stirred kettles with stirrers passing close to the wall or cooling-disk crystallizers, these apparatuses have no means for avoiding crystal layers on the heat-transfer surfaces. If, during operation, a state is reached in which the heat transfer resistance assumes too high a value owing to formation of crystal layers, switching to a second apparatus is effected. During the operation time in the second apparatus, the first apparatus is regenerated (preferably by melting off the crystal layer or flushing the apparatus with unsaturated solution). If too high a heat transfer resistance is reached in the second apparatus, the system is switched back to the first apparatus, etc. This variant can also be operated cyclically with more than two apparatuses. Moreover, the crystallization can be carried out by conventional evaporation of the solution under reduced pressure.

Advantageously, the temperature of the solution during the crystallization (a) is from −15 to +14° C., in particular from 0 to +14° C., while the temperature in the crystallization (c) is from −30 to +5° C., in particular from −15 to 0° C. The solids content in the crystallizer in both crystallizations (a) and (c) is advantageously from 0 to 85, preferably from 25 to 80, g of solid/100 g.

The method of separating the acrylic acid crystals or methacrylic acid crystals obtained after the crystallization (a) and (c) is not subject to any particular restrictions. For the layer crystallization or the static crystallization, the separation of the crystals from the mother liquor can be effected in the crystallization apparatus itself since the crystals are fixed in the apparatus and the mother liquor can be removed by allowing it to flow out of the apparatus. The crystals are removed from the crystallization apparatus by melting the crystals and then allowing the melt to flow out. For the suspension crystallization, all known solid-liquid separation methods are suitable. Preferably, the crystals are separated from the mother liquor by filtration and/or centrifuging. The filtration or centrifuging is advantageously preceded by preliminary thickening of the suspension, for example by means of hydrocyclones. All known centrifuges which operate batchwise or continuously are suitable for the centrifuging. Reciprocating centrifuges which can be operated in one stage or a plurality of stages are most advantageously used. In addition, helical screen centrifuges or helical conveyor centrifuges (decanters) are also suitable. Filtration is advantageously effected by means of suction filters which are operated continuously or batchwise, with or without a stirrer, or by means of belt filters. In general, the filtration can be carried out under superatmospheric or reduced pressure. During and/or after the solid-liquid separation, further process steps for increasing the purity of the crystals or the crystal cake can be provided. In a particularly advantageous embodiment of the invention, the separation of the crystals from the mother liquor is followed by one-stage or multistage washing and/or sweating of the crystals or of the crystal cake. The wash liquid used here is not subject to any restriction. Advantageously, however, washing is effected with pure product, i.e. with a liquid which contains acrylic acid or methacrylic acid whose purity is higher than that of the crystal cake to be washed. Washing with water is also possible. The washing can be effected in apparatuses customary for this purpose, such as wash columns, in which the separation of the mother liquor and the washing are carried out in one apparatus, in centrifuges, which can be operated in one stage or a plurality of stages, or in suction filters or belt filters. The washing can be carried out on centrifuges or belt filters in one stage or a plurality of stages, it being possible to pass the wash liquid countercurrent to the crystal cake. In addition, it is possible to provide sweating for increasing the purity of the crystals, which involves local melting of contaminated regions. The sweating is particularly preferably carried out on centrifuges or belt filters, but a combination of washing and sweating in one apparatus may also be suitable.

If the crystallization (a) is carried out in a plurality of stages, the mother liquor with the lowest purity is preferably fed to the distillation (b). It is also possible to combine the mother liquors of some or all of the crystallization stages of crystallization (a) and then to feed them to the distillation (b). If the crystallization (c) is carried out in a plurality of stages, the crystallization residue with the lowest purity is preferably removed and the crystals with the highest purity are fed to the crystallization (a).

The amount of mother liquor from step (a), which is fed to the distillation (b) is preferably from 5 to 100, in particular from 50 to 100, most preferably from 90 to 100,% by weight. Mother liquor from step (a) which is not fed to the distillation (b) is expediently fed to the crystallization (c).

In principle, any distillation column can be used for the distillation (b). The distillation, distillation stage or the distillation step (b) can be carried out in one stage or a plurality of stages. In a multistage or fractional distillation (also referred to as rectification), which is advantageously carried out in rectification columns, a column having sieve trays, for example dual-flow trays or crossflow sieve trays of metal, is used. The distillation can also be carried out by means of an evaporator and of a downstream condenser. Thin-film evaporators in the form of falling-film evaporators or agitated-film evaporators are particularly preferred here. The condensers used are the conventional condensers, which are not subject to any restrictions. In a one-stage distillation, a simple evaporator, for example a still, and a conventional condenser are expediently used.

A stabilizer, such as phenothiazine or another stabilizer disclosed in, for example, EP-A-0 765 856, may be added to the acrylic acid to stabilize it and to prevent polymerization during the distillation (b), provided that such a stabilizer is not yet or is not present in sufficient amounts.

The amount of top product from the distillation (b) which is fed to the crystallization (c) is preferably from 5 to 100, in particular from 50 to 100, most preferably from 80 to 100,% by weight of top product. Top product not fed to the crystallization (c) is advantageously fed to the crystallization (a). At least a part of the distillation residue, preferably from 5 to 100, in particular from 5 to 50, % by weight of the distillation residue from the distillation (b), is removed from the process, while from 0 to 95, in particular from 50 to 95,% by weight of the distillation residue is recycled to the preparation of the acrylic acid or methacrylic acid, preferably to the catalytic gas-phase oxidation for the preparation of the acrylic acid or methacrylic acid, as has been described above.

The invention has the advantage that the desired acid is obtained in high purity and at the same time in a high yield. In contrast to EP-A-0 675 100, two crystallizations are carried out according to the invention and are linked to one another in that the crystals of the second crystallization are fed to the first crystallization so that the second crystallization may be regarded as a sort of stripping stages of the first crystallization. At the same time, the invention envisages the partial removal of the distillation residue as well as the removal of a crystallization residue from the process. In comparison, EP-A-0 675 100 discloses only a crystallization which, if required, may be carried out as a multistage procedure with purification stages, and the removal of residue from the process at only one point, i.e. either from the crystallization or from the distillation. Compared with EP-A-0 675 100, the invention therefore has the advantage that substances which are difficult to remove from the process by distillation and crystallization can be removed simultaneously. For example, propionic acid, which is difficult or impossible to separate off by distillation, is removed via the crystallization residue, while substances which are readily precipitated together with the desired acid in the crystallization stage (e.g. phenothiazine, maleic acid) and would thus reduce the separation effect of the crystallization are removed from the process, before their solubility limit is exceeded, by removing the distillation residue.

The FIGURE describes a preferred embodiment of the novel process. The mixture containing the acrylic acid or methacrylic acid is fed via supply line 1 to the crystallization (a). After the crystallization (a) and a solid-liquid separation (not shown) have been carried out, product crystals, which are removed via line 2, and a mother liquor, which is fed via line 3 and at least partly via line 4 to the distillation (b) are obtained. Mother liquor from line 3 which is not fed to the distillation (b) is fed via line 5 to the crystallization (c). The distillation (b) gives a distillation residue, which is removed from the process via line 7, and a top product, which is removed from the distillation via line 6. At least a part of the top product from line 6 is fed via line 9 to the crystallization (c). Top product from line 6 which is not fed to the crystallization (c) is fed via line 8 to the crystallization (a). After the crystallization (c) and a solid-liquid separation (not shown) have been carried out, crystals, which are fed via line 10 to the crystallization (a), and a crystallization residue, which is removed from the process via line 11, are obtained.

The example which follows and which constitutes a preferred embodiment of the invention illustrates the invention.

EXAMPLE

A stream according to the starting composition stated below in Table 1 was subjected to a five-stage crystallization (crystallization (a)) with two purification stages and three stripping stages, all stages being carried out dynamically. The solids content in the crystallizer was 72 g/100 g in each case. After the solid-liquid separation, product crystals were obtained in the 2nd purification stage (i.e. the purification stage of highest purity) and a mother liquor according to the following Table 1 was obtained in the 3rd stripping stage (i.e. the stripping stage of lowest purity).

TABLE 1

| Streams | Starting composition | Product crystals | Mother liquor |
| --- | --- | --- | --- |
| Acrylic acid | 99.48% by wt. | 99.94 | 77.63% by wt. |
| Acetic acid | 2600 ppm | 374 ppm | 13.285% by wt. |
| Propionic acid | 358 ppm | 99 ppm | 1.348% by wt. |
| Water | 460 ppm | 91 ppm | 2.002% by wt. |
| Phenothiazine | 420 ppm | 1 ppm | 1.192% by wt. |
| Furan II aldehyde | 335 ppm | 0.5 ppm | 1.307% by wt. |
| Others | 0.1027% by wt. | 35 ppm | 3.236% by wt. |

The mother liquor according to Table 1 was fed in an amount of 100% to a distillation (b). This distillation was carried out in one stage in a thin-film evaporator. The vapor formed here was condensed by conventional methods. The ratio of top product to mother liquor in the evaporator was 80 g/100 g. Table 2 below shows the composition of the top product obtained in the distillation (b) and of the distillation residue.

TABLE 2

| Streams | Top product | Residue |
| --- | --- | --- |
| Acrylic acid | 77.74% by wt. | 77.17% by wt. |
| Acetic acid | 15.41% by wt. | 4.783% by wt. |
| Propionic acid | 1.335% by wt. | 1.402% by wt. |
| Water | 2.382% by wt. | 0.481% by wt. |
| Phenothiazine | 0.107% by wt. | 5.530% by wt. |
| Furan II aldehyde | 1.137% by wt. | 1.9864% by wt. |
| Others | 1.889% by wt. | 8.648% by wt. |

The residue from the distillation (b) was discarded whereas the top product was fed in an amount of 100% to a crystallization (c). This crystallization (c) was carried out in two static stages (i.e. a purification stage and a stripping stage). The solids content was 50 g/100 g in each case. Here, the following crystals were obtained in the purification stage and the following residue in the stripping stage:

TABLE 3

| Streams | Crystals | Residue |
| --- | --- | --- |
| Acrylic acid | 83.28% by wt. | 61.12% by wt. |
| Acetic acid | 12.134% by wt. | 25.24% by wt. |
| Propionic acid | 1.079% by wt. | 2.103% by wt. |
| Water | 1.674% by wt. | 4.507% by wt. |
| Phenothiazine | 0.091% by wt. | 1.146% by wt. |
| Furan II aldehyde | 0.677% by wt. | 2.518% by wt. |
| Others | 1.065% by wt. | 3.366% by wt. |

The crystals according to Table 3 were fed in an amount of 100% to the crystallization stage (a) while the residue according to Table 3 was discarded.

As shown in particular in Table 1 of the example, an acrylic acid of relatively high purity can be prepared in—owing to the recycling—high yield by the novel process.

We claim:
1. A process for the purification of acrylic acid or methacrylic acid by crystallization and distillation, which comprises the following steps:
   (a) crystallization of a mixture containing the acrylic acid or methacrylic acid with formation of product crystals having a higher concentration of acrylic acid or methacrylic acid and of a mother liquor,
   (b) distillation of at least part of the mother liquor from step (a) with formation of a distillation residue, which is at least partly removed, and of a top product,

(c) crystallization of at least part of the top product from step (b) with formation of a crystallization residue, which is removed, and of crystals and (d) recycling of the crystals from step (c) to the crystallization (a).

2. A process as claimed in claim 1, wherein the mixture containing the acrylic acid or methacrylic acid contains from 50 to 99.95% by weight, based on the mixture, of acrylic acid or methacrylic acid.

3. A process as claimed in claim 1, wherein the crystallization (a) and the crystallization (c) are each carried out in one stage or a plurality of stages.

4. A process as claimed in claim 1, wherein from 5 to 100% by weight of the mother liquor from step (a) are distilled in step (b).

5. A process as claimed in claim 1, wherein the distillation (b) is carried out in one stage or a plurality of stages (as a fractional distillation).

6. A process as claimed in claim 1, wherein from 5 to 100% by weight of the top product from step (b) are crystallized in step (c).

7. A process as claimed in claim 1, wherein the mixture containing the acrylic acid or methacrylic acid is prepared by catalytic gas-phase oxidation of a compound selected from the group consisting of $C_3$-/$C_4$-alkanes, -alkenes, -alkanols, -alkanals, precursors thereof, and mixtures thereof.

8. A process as claimed in claim 1, wherein from 0 to 95% by weight of the residue of the distillation (b) are recycled to the process for the preparation of the acrylic acid or methacrylic acid.

9. A process for the purification of acrylic acid or methacrylic acid by crystallization and distillation, which comprises the following steps:

(a) crystallization of a mixture containing the acrylic acid or methacrylic acid with formation of product crystals having a higher concentration of acrylic acid or methacrylic acid and of a mother liquor, (b) distillation of at least part of the mother liquor from step (a) with formation of a distillation residue, which is at least partly removed, and of a top product, (c) crystallization of at least part of the top product from step (b) with formation of a crystallization residue, which is removed, and of crystals and (d) recycling of the crystals from step (c) to the crystallization (a), wherein the crystallization (a) is carried out as a dynamic crystallization and the crystallization (c) as a static crystallization.

10. A process as claimed in claim 9, wherein the mixture containing the acrylic acid or methacrylic acid contains from 50 to 99.95% by weight, based on the mixture, of acrylic acid or methacrylic acid.

11. A process as claimed in claim 9, wherein from 5 to 100% by weight of the mother liquor from step (a) are distilled in step (b).

12. A process as claimed in claim 9, wherein from 5 to 100% by weight of the top product from step (b) are crystallized in step (c).

13. A process as claimed in claim 9, wherein the mixture containing the acrylic acid or methacrylic acid is prepared by catalytic gas-phase oxidation of a compound selected from the group consisting of $C_3$-/$C_4$-alkanes, -alkenes, -alkanols, -alkanals, precursors thereof, and mixtures thereof.

14. A process as claimed in claim 9, wherein from 0 to 95% by weight of the residue of the distillation (b) are recycled to the process for the preparation of the acrylic acid or methacrylic acid.

15. A process for the purification of acrylic acid or methacrylic acid by crystallization and distillation, which comprises the following steps:

(a) crystallization of a mixture containing the acrylic acid or methacrylic acid with formation of product crystals having a higher concentration of acrylic acid or methacrylic acid and of a mother liquor, (b) distillation of at least part of the mother liquor from step (a) with formation of a distillation residue, which is at least partly removed, and of a top product, (c) crystallization of at least part of the top product from step (b) with formation of a crystallization residue, which is removed, and of crystals and (d) recycling of the crystals from step (c) to the crystallization (a), wherein a crystallization selected from the group consisting of crystallization (a), crystallization (c), and a combination thereof is carried out as a combined dynamic and static crystallization, the residue of the dynamic crystallization being fed to the static crystallization and the crystals of the static crystallization being fed to the dynamic crystallization.

16. A process as claimed in claim 15, wherein the mixture containing the acrylic acid or methacrylic acid contains from 50 to 99.95% by weight, based on the mixture, of acrylic acid or methacrylic acid.

17. A process as claimed in claim 15, wherein from 5 to 100% by weight of the mother liquor from step (a) are distilled in step (b).

18. A process as claimed in claim 15, wherein from 5 to 100% by weight of the top product from step (b) are crystallized in step (c).

19. A process as claimed in claim 15, wherein the mixture containing the acrylic acid or methacrylic acid is prepared by catalytic gas-phase oxidation of a compound selected from the group consisting of $C_3$-/$C_4$alkanes, -alkenes, -alkanols, -alkanals, precursors thereof, and mixtures thereof.

20. A process as claimed in claim 15, wherein from 0 to 95% by weight of the residue of the distillation (b) are recycled to the process for the preparation of the acrylic acid or methacrylic acid.

* * * * *